US00PP19662P2

(12) United States Plant Patent
Hop

(10) Patent No.: US PP19,662 P2
(45) Date of Patent: Jan. 27, 2009

(54) ***AGASTACHE* PLANT NAMED 'HEATWAVE'**

(50) Latin Name: ***Agastache* sp.**
Varietal Denomination: Heatwave

(76) Inventor: Margareth Hop, P.P.O. BV Professor van Slogterenweg 2, Lisse (NL), NL 2161 DW ( * ) Notice: Subject to any disclaimer, the term of this patent is extended or adjusted under 35 U.S.C. 154(b) by 0 days.

(21) Appl. No.: 11/891,594

(22) Filed: Aug. 13, 2007

(51) Int. Cl.
*A01H 5/00* (2006.01)

(52) U.S. Cl. ..... Plt./399

(58) Field of Classification Search ..... Plt./399
See application file for complete search history.

(56) References Cited

U.S. PATENT DOCUMENTS

PP13,673 P2 * 3/2003 Sinning ..... Plt./258
PP16,023 P2 * 10/2005 Moonen ..... Plt./399

* cited by examiner

*Primary Examiner*—Wendy C. Haas

(57) ABSTRACT

A new cultivar of *Agastache* named 'HEATWAVE' that is distinguished by large bright magenta flowers and a broad upright growth habit. In combination, these characteristics set 'HEATWAVE' apart from all other existing varieties of *Agastache* known to the inventor.

3 Drawing Sheets

Genus: *Agastache.*
Species: sp.
Denomination: 'HEATWAVE'.

BACKGROUND OF THE INVENTION

The present invention relates to a new and distinct cultivar of *Agastache,* commonly known as giant hyssop. This hardy perennial is grown for use as an ornamental landscape plant. The new invention will be referred to hereinafter by the cultivar name 'HEATWAVE'.

'HEATWAVE' was discovered by the inventor as a chance seedling in a group of seedlings grown from seeds received in a seed exchange as *Monarda austromontana* but subsequently identified as unnamed *Agastache cana* or *Agastache mexicana.* The pollen parent is unknown. The initial discovery occurred in 1996 at the inventor's nursery in Boskoop, The Netherlands.

The new variety of *Agastache* 'HEATWAVE' is an herbaceous perennial characterized by its height and large bright magenta flowers. 'HEATWAVE' is more floriferous than other cultivars and has better winter hardiness.

The closest comparison plants to 'HEATWAVE' known to the inventor are *Agastache* 'Heather Queen' (unpatented), *Agastache* 'Sinning' (U.S. Plant Pat. No. 13,673), and *Agastache* 'Kiegabi' (U.S. Plant Pat. No. 16,023). 'HEATWAVE' is twice the height of 'Heather Queen' or 'Sinning'. 'HEATWAVE' has a darker flower color than 'Kiegabi' and is more winter hardy than most other *Agastache cana* or *mexicana* cultivars.

The first asexual reproduction of 'HEATWAVE' was accomplished in 2001 by the inventor using the method of stem cuttings. The inventor has determined that 'HEATWAVE' is a stable variety which reproduces true to type in all successive generations of asexual reproduction.

SUMMARY OF THE INVENTION

The following traits have been repeatedly observed and represent the distinguishing characteristics of 'HEATWAVE'. These traits in combination distinguish 'HEATWAVE' from all other existing varieties of *Agastache.* 'HEATWAVE' has not been tested under all possible conditions and phenotypic differences may be observed with variations in environmental, climatic, and cultural conditions, however, without any variance in genotype.

1. *Agastache* 'HEATWAVE' exhibits a broad upright growth habit.
2. *Agastache* 'HEATWAVE' exhibits bright magenta-red flowers.
3. *Agastache* 'HEATWAVE' is hardy to USDA Zone 8A.
4. *Agastache* 'HEATWAVE' is an herbaceous perennial.
5. *Agastache* 'HEATWAVE' is approximately 89 cm in height and 66 cm in width at maturity.

BRIEF DESCRIPTION OF THE DRAWINGS

The accompanying drawings illustrate the distinguishing traits of the new cultivar 'HEATWAVE'. The drawings have been made from photographs which were taken in spring and summer using plants that were 2 years old, grown out of doors in The Netherlands.

The drawing labeled as FIG. 1 depicts the entire aboveground growth.

Figure 1:
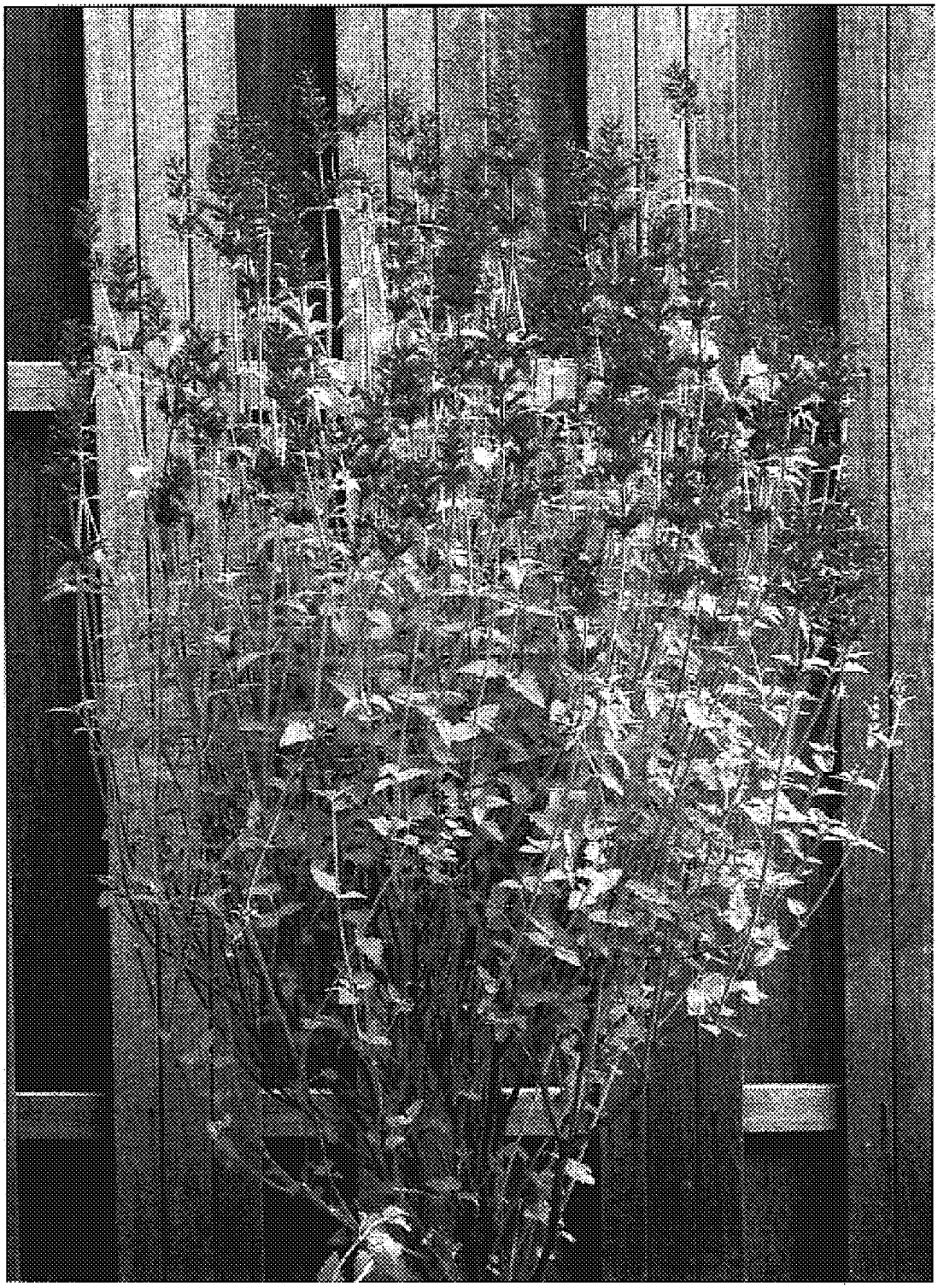
Figure 2:
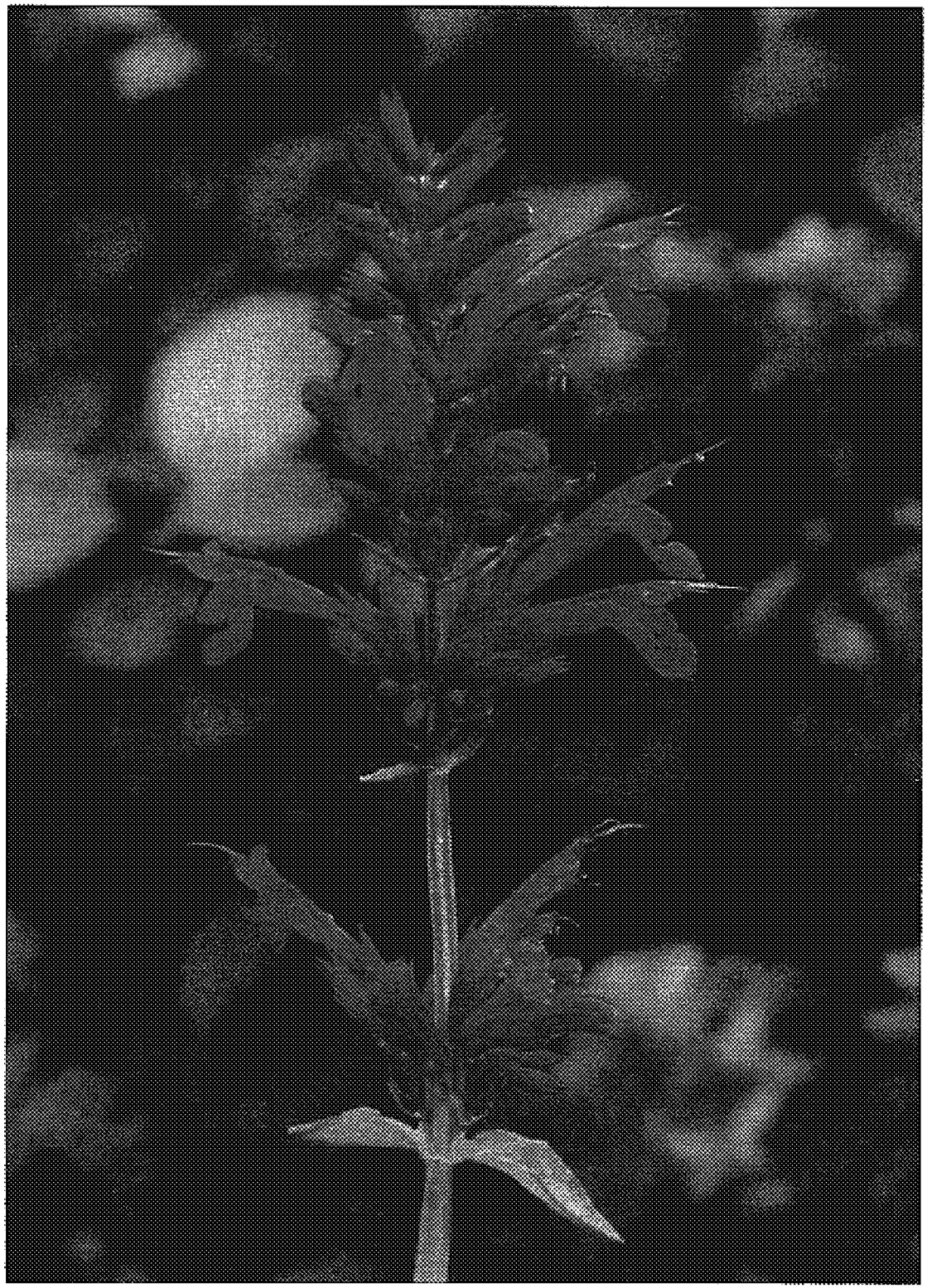
Figure 3:
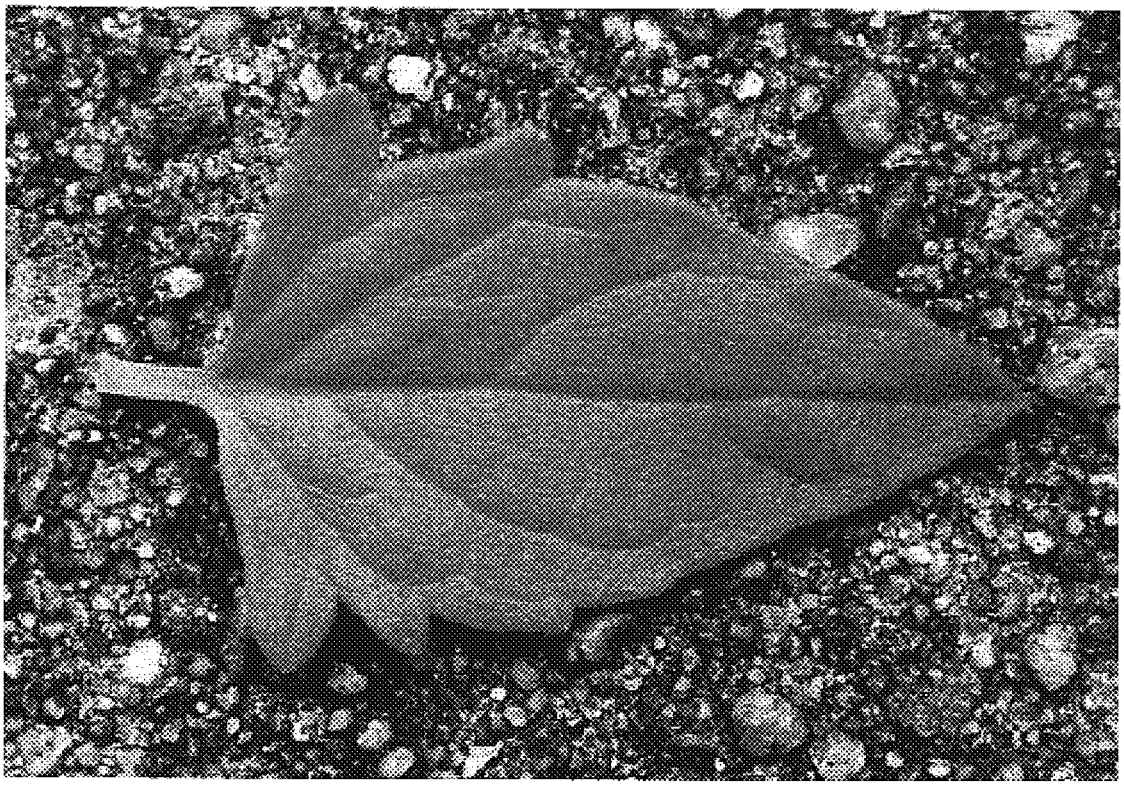

The drawing labeled as FIG. 2 illustrates a close-up view of a single inflorescence.

The drawings have been made from photographs taken by conventional photographic techniques and although flower and foliage colors in the photographs may appear different from actual colors due to light reflectance, they are as accurate as possible by conventional photography.

BOTANICAL DESCRIPTION OF THE PLANT

The following is a detailed botanical description of the new *Agastache* cultivar named 'HEATWAVE'. Observations, measurements, values and comparisons have been collected in summer in Boskoop, Netherlands from plants that were two years old and grown out of doors in a 5 liter container. Color determinations are made in accordance with the 2001 edition of The Royal Horticultural Society's Colour Chart, except where general color terms of ordinary dictionary significance are used. The growing requirements of the new variety are similar to the species and there are no known growing problems, diseases or pests.

Botanical classification: *Agastache* 'HEATWAVE'.
Common name: Giant hyssop.
Parentage: Discovered in a crop of seedlings sown from seeds identified as *Agastache cana* or *Agastache mexicana;* pollen parent unknown.
Propagation method: Stem cuttings.
Rooting habit: Fibrous.
Time to develop roots: 2–3 weeks at a rooting medium temperature of 20° C.–25° C.
Crop time: Approximately 20 weeks to produce saleable plants in a 9 cm to 11 cm pot.
Growth habit: Broad upright.
Overall shape: Inverted triangle.
Use: Ornamental landscape plant.
Type: Herbaceous perennial.
Vigor: Moderately vigorous.
Height of plant: 89 cm in height.
Width of plant: 66 cm in width.
Growth rate: Approximately 20 cm per month (in spring).
Cultural requirements: Plant in full sun and well-drained soil.
Hardiness: USDA Zone 8a.
Stem:
*Branching habit.*—Main stems grow from base and have lateral branches.
*Pinching.*—Required to improve branching.
*Number of lateral branches.*—An average of 70 after two pinchings.
*Lateral branch dimensions.*—An average of 42.5 cm in length and 3 mm in diameter.
*Internode length.*—An average of 10 cm.
*Aspect.*—Quadrangular, sometimes ribbed lengthways, but not winged.
*Appearance.*—Dull.
*Strength.*—Strong.
*Color.*—143A.
*Pubescence.*—Densely covered with very short green-white hairs, average 0.1 mm in length; too small to be color-measured.
*Fragrance.*—Pleasantly aromatic; reminiscent of licorice.
Foliage:
*Leaves.*—Arrangement: Opposite. Type: Single. Quantity of leaves per lateral branch: An average of 8 (4 pairs). Shape: Ovate to deltoid. Apex: Acute. Base: Cordate to truncate. Dimensions: An average of 3.2 cm in length and 2.4 cm in width. Texture: Slightly glossy and slightly rugose, due to the impressed veining. Pubescence: None. Margin: Coarsely serrate with an average of 2 teeth per cm. Venation: Pinnate. Color of young leaf (adaxial): 1443B to 144A. Color of young leaf (abaxial): 143C. Color of mature leaf (adaxial): 137A and 137B. Color of mature leaf (abaxial): 138B. Vein color (adaxial): 138B. Vein color (abaxial): 138C.
*Attachment.*—Petiolate.
*Petiole dimensions.*—An average of 7 mm in length and 1 mm in diameter.
*Petiole color.*—144B.
*Durability of foliate to stress.*—High.
*Fragrance.*—Pleasant and spicy.
Flower:
*Arrangement.*—Terminal compound verticillasters.
*Inflorescence.*—Type: Compound verticillasters. Dimensions: An average of 13.1 cm in height and 4.9 cm in width. Quantity of flowers per inflorescence: An average of 150. Quantity of flowers per plant: An average of 10,000. Bloom period: Late summer into autumn. Time to flower: Approximately 10 months. Rate of flower opening: Approximately 5% of flowers open at once. Fragrance: None.
*Buds.*—Dimensions: An average of 1.6 cm in length and 3.2 mm in diameter. Shape: Narrow, oblanceolate and curved. Color: 71A.
*Flowers.*—Aspect: Outward. Shape: Labiate. Dimensions: An average of 2.8 cm in height and 8 mm in diameter.
*Longevity on plant.*—Approximately 5 days.
*Longevity off plant.*—Not-applicable.
*Persistent or self-cleaning.*—Self-cleaning.
*Petals.*—Appearance: Labiate with one upper lip and one lower lip. Texture: Slightly glossy, densely covered with very short glandular hairs, same color as corolla. Arrangement: Labiate. Number: Labiate, thus fused (only one upper lip and one lobed under lip visible). Fused: Only upper 15% of petals is free. Shape: Upper lip narrow oblanceolate; under lip spathulate with one large lobe and a smaller lobe on each side. Margin: Entire. Tip: Upper lip emarginated; under lip praemorse. Dimensions: An average of 2.4 cm in length; an average of 4 mm in width for upper lip and 8 mm in width for lower lip. Color when opening (both surfaces): 71A to 72A. Color when fully open (both surfaces): 72B Color when fading: No fading. Petaloids: None.
*Sepals.*—Number: 5 Appearance: Dull, tubular. Arrangement: Rotate, tubular. Shape: Fused, tubular, tips free. Margin: Fused, margins of free part entire. Tip: Acuminate. Base: Fused into tubular shape. Dimensions: An average of 1.1 cm in length and 1.3 mm in width (measured at the base of the free tip). Color (adaxial surface, immature and mature): N79C. Color (abaxial surface, immature and mature): N79B and N79C.
*Calyx shape.*—Tubular.
*Calyx dimensions.*—An average of 1.1 cm in length and 4 mm in diameter.
*Peduncle.*—Dimensions: An average of 12.3 cm in length and 2 mm in diameter. Angle: Straight on top of lateral stem (0°). Strength: Strong. Color: 147A with a touch of 187B.
*Pedicel.*—Dimensions: An average of 4 mm in length and 0.5 mm in diameter. Average angle: 25° from the vertical. Strength: Moderate. Color: N79B and N79C.
Reproductive organs:
*Stamen number.*—4, paired.
*Anther shape.*—Basifixed, broad oval.
*Average anther size.*—0.8 mm.
*Average length of longest pair of filaments.*—2.9 cm.
*Anther color.*—N79C.
*Amount of pollen.*—Low.
*Pollen color.*—156D.
*Pistil number.*—1.

*Pistil length.*—An average of 3.0 cm.
*Stigma shape.*—Cleft.
*Stigma color.*—N79B and N79C.
*Style lengths An average of* 2.8 cm.
*Style color.*—79B, lighter towards the base.
*Ovary color.*—150B.

Fruit and seed: None have been observed.

It is claimed:

1. A new and distinct cultivar of *Agastache* plant named 'HEATWAVE' as described and illustrated.

* * * * *